United States Patent [19]

Schmolke et al.

[11] Patent Number: 6,020,195
[45] Date of Patent: Feb. 1, 2000

[54] ANTIBODIES AGAINST HEPATITIS G VIRUS AND THEIR USE FOR THE DIAGNOSTIC DETECTION OF HGV AND AS A THERAPEUTIC AGENT

[75] Inventors: Susanne Schmolke; Michael Tacke, both of Penzberg; Christa Hübner-Parajsz, Tutzing; Alfred Engel, Penzberg; Beatus Ofenloch-Hähnle, Polling, all of Germany

[73] Assignee: Roche Diagnostics GmbH, Mannheim, Germany

[21] Appl. No.: 08/932,823

[22] Filed: Sep. 18, 1997

[30] Foreign Application Priority Data

Sep. 18, 1996 [DE] Germany ............................ 196 38 133
Oct. 22, 1996 [DE] Germany ............................ 196 43 650

[51] Int. Cl.$^7$ .............................. C07K 16/08; C12N 5/20
[52] U.S. Cl. ........................................ 435/339; 530/388.3
[58] Field of Search .................................. 424/149, 161.1, 424/178.1, 130.1, 147.1, 159.1; 530/388.3, 389.4; 435/339

[56] References Cited

U.S. PATENT DOCUMENTS 5,766,840  6/1998  Kim et al. ..................................... 435/5

OTHER PUBLICATIONS

International Publication No. WO 95/32291, published Nov. 30, 1995.
Davis et al., "Use of plasmid DNA for direct gene transfer and immunization", Annals of the New York Academy of Sciences, vol. 772, Nov. 22, 1995, pp. 21–29.
International Publication No. WO 95/32292, published Nov. 30, 1995.
Linnen et al., "Molecular cloning and disease association of hepatits G virus: a transfusion–transmissible agent", Science, vol. 271, No. 5248, Jan. 26, 1996, pp. 505–508.
International Publication No. WO 94/18217, published Aug. 18, 1994.
International Publication No. WO 93/04205, published Mar. 4, 1993.
Kim et al., "Molecular characterization of the hepatitis G virus", Journal of Viral Hepatitis, 1974, 4, pp. 77–79.

*Primary Examiner*—Donna C. Wortman
*Assistant Examiner*—Brenda G. Brumback
*Attorney, Agent, or Firm*—Nikaido Marmelstein Murray & Oram, LLP

[57] ABSTRACT

The present invention concerns an antibody against a hepatitis G virus antigen as well as a fragment of this antibody. The invention additionally concerns hybridoma cell lines as well as a conjugate that contains this antibody or the antibody fragment coupled to a biological molecule. Finally the present invention concerns the use of the antibody for the diagnostic detection of hepatitis G virus.

6 Claims, 2 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1302 base pairs
        (B) TYPE: nucleic acid
        (C) STRANDEDNESS: both
        (D) TOPOLOGY: linear (vi) ORIGINAL SOURCE:
        (A) ORGANISM: Hepatitis G Virus (vii) IMMEDIATE SOURCE:
        (B) CLONE: E1TM (ix) FEATURE:
        (A) NAME/KEY: CDS
        (B) LOCATION:13..1290

(xi) SEQUENCE DESCRIPTION: SEQ ID NO: 1:

```
GAATTCACCA CC ATG GGG GTG CAC GAA TGT CCT GCC TGG CTG TGG CTT             48
              Met Gly Val His Glu Cys Pro Ala Trp Leu Trp Leu
                1               5                      10

CTC CTG TCC CTG CTG TCG CTC CCT CTG GGC CTC CCA GTC CTG GGC GAC           96
Leu Leu Ser Leu Leu Ser Leu Pro Leu Gly Leu Pro Val Leu Gly Asp
            15                  20                  25

TAC AAG GAC GAT GAC GAT AAG GCG GCC GCG ATG TCG CAA GGC GCC CCT          144
Tyr Lys Asp Asp Asp Asp Lys Ala Ala Ala Met Ser Gln Gly Ala Pro
        30                  35                  40

GCC TCC GTT TTG GGG TCA CGC CCC TTT GAC TAC GGG TTG ACT TGG CAG          192
Ala Ser Val Leu Gly Ser Arg Pro Phe Asp Tyr Gly Leu Thr Trp Gln
 45                 50                  55                  60

ACC TGC TCT TGC AGG GCC AAC GGT TCG CGT TTT TCG ACT GGG GAG AAG          240
Thr Cys Ser Cys Arg Ala Asn Gly Ser Arg Phe Ser Thr Gly Glu Lys
                65                  70                  75

GTG TGG GAC CGT GGG AAC GTT ACG CTT CAG TGT GAC TGC CCT AAC GGC          288
Val Trp Asp Arg Gly Asn Val Thr Leu Gln Cys Asp Cys Pro Asn Gly
            80                  85                  90

CCC TGG GTG TGG TTG CCA GCC TTT TGC CAA GCA ATC GGC TGG GGT GAC          336
Pro Trp Val Trp Leu Pro Ala Phe Cys Gln Ala Ile Gly Trp Gly Asp
        95                  100                 105

CCC ATC ACT TAT TGG AGC CAC GGG CAA AAT CAG TGG CCC CTT TCA TGC          384
Pro Ile Thr Tyr Trp Ser His Gly Gln Asn Gln Trp Pro Leu Ser Cys
    110                 115                 120

CCC CAG TAT GTC TAT GGG TCT GCT ACA GTC ACT TGC GTG TGG GGT TCC          432
Pro Gln Tyr Val Tyr Gly Ser Ala Thr Val Thr Cys Val Trp Gly Ser
125                 130                 135                 140

GCT TCT TGG TAT GCC TCC ACC AGT GGT CGC GAC TCG AAG ATA GAT GTG          480
Ala Ser Trp Tyr Ala Ser Thr Ser Gly Arg Asp Ser Lys Ile Asp Val
                145                 150                 155

TGG AGT TTA GTG CCA GTT GGC TCT GCC ACC TGC ACC ATA GCC GCA CTT          528
Trp Ser Leu Val Pro Val Gly Ser Ala Thr Cys Thr Ile Ala Ala Leu
            160                 165                 170

GGA TCA TCG GAT CGC GAC ACG GTG CCT GGG CTC TCC GAG TGG GGA ATC          576
```

-continued

```
                Gly Ser Ser Asp Arg Asp Thr Val Pro Gly Leu Ser Glu Trp Gly Ile
                        175                 180                 185

CCG TGC GTG ACG TGT GTT CTG GAC CGT CGG CCT GCT TCA TGC GGC ACC           624
Pro Cys Val Thr Cys Val Leu Asp Arg Arg Pro Ala Ser Cys Gly Thr
        190                 195                 200

TGT GTG AGG GAC TGC TGG CCC GAG ACC GGG TCG GTT AGG TTC CCA TTC           672
Cys Val Arg Asp Cys Trp Pro Glu Thr Gly Ser Val Arg Phe Pro Phe
205                 210                 215                 220

CAT CGG TGC GGC GTG GGG CCT CGG CTG ACA AAG GAC TTG GAA GCT GTG           720
His Arg Cys Gly Val Gly Pro Arg Leu Thr Lys Asp Leu Glu Ala Val
                225                 230                 235

CCC TTC GTC AAT AGG ACA ACT CCC TTC ACC ATT AGG GGG CCC CTG GGC           768
Pro Phe Val Asn Arg Thr Thr Pro Phe Thr Ile Arg Gly Pro Leu Gly
        240                 245                 250

AAC CAG GGC CGA GGC AAC CCG GTG CGG TCG CCC TTG GGT TTT GGG TCC           816
Asn Gln Gly Arg Gly Asn Pro Val Arg Ser Pro Leu Gly Phe Gly Ser
                255                 260                 265

TAC GCC ATG ACC AGG ATC CGA GAT ACC CTA CAT CTG GTG GAG TGT CCC           864
Tyr Ala Met Thr Arg Ile Arg Asp Thr Leu His Leu Val Glu Cys Pro
        270                 275                 280

ACA CCA GCC ATC GAG CCT CCC ACC GGG ACG TTT GGG TTC TTC CCC GGG           912
Thr Pro Ala Ile Glu Pro Pro Thr Gly Thr Phe Gly Phe Phe Pro Gly
285                 290                 295                 300

ACG CCG CCT CTC AAC AAC TGC ATG CTC TTG GGC ACG GAA GTG TCC GAG           960
Thr Pro Pro Leu Asn Asn Cys Met Leu Leu Gly Thr Glu Val Ser Glu
                305                 310                 315

GCA CTT GGG GGG GCT GGC CTC ACG GGG GGG TTC TAT GAA CCC CTG GTG          1008
Ala Leu Gly Gly Ala Gly Leu Thr Gly Gly Phe Tyr Glu Pro Leu Val
        320                 325                 330

CGC AGG TGT TCG GAG CTG ATG GGA AGC CGA AAT CCG GTT TGT CCG GGG          1056
Arg Arg Cys Ser Glu Leu Met Gly Ser Arg Asn Pro Val Cys Pro Gly
                335                 340                 345

TTT GCA TGG CTC TCT TCG GGC AGG CCT GAT GGG TTT ATA CAT GTC CAG          1104
Phe Ala Trp Leu Ser Ser Gly Arg Pro Asp Gly Phe Ile His Val Gln
350                 355                 360

GGT CAC TTG CAG GAG GTG GAT GCA GGC AAC TTC ATC CCG CCC CCG CGC          1152
Gly His Leu Gln Glu Val Asp Ala Gly Asn Phe Ile Pro Pro Pro Arg
365                 370                 375                 380

TGG TTG CTC TTG GAC TTT GTA TTT GTC CTG TTA TAC CTG ATG AAG CTG          1200
Trp Leu Leu Leu Asp Phe Val Phe Val Leu Leu Tyr Leu Met Lys Leu
                385                 390                 395

GCT GAG GCA CGG TTG GTC CCG CTG ATC TTG CTG CTA TGG TGG TGG              1248
Ala Glu Ala Arg Leu Val Pro Leu Ile Leu Leu Leu Trp Trp Trp
        400                 405                 410

GTG AAC CAG CTG GCA GTC CTA GGG CTG CCG GCT GTG GAA GCC                  1290
Val Asn Gln Leu Ala Val Leu Gly Leu Pro Ala Val Glu Ala
                415                 420                 425

TAATAGTCTA GA                                                            1302
```

(2) INFORMATION FOR SEQ ID NO: 2:

(i) SEQUENCE CHARACTERISTICS:
        (A) LENGTH: 426 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gly Val His Glu Cys Pro Ala Trp Leu Trp Leu Leu Leu Ser Leu
 1               5                  10                  15
```

-continued

```
Leu Ser Leu Pro Leu Gly Leu Pro Val Leu Gly Asp Tyr Lys Asp Asp
         20              25              30
Asp Asp Lys Ala Ala Ala Met Ser Gln Gly Ala Pro Ala Ser Val Leu
         35              40              45
Gly Ser Arg Pro Phe Asp Tyr Gly Leu Thr Trp Gln Thr Cys Ser Cys
 50              55              60
Arg Ala Asn Gly Ser Arg Phe Ser Thr Gly Glu Lys Val Trp Asp Arg
 65              70              75              80
Gly Asn Val Thr Leu Gln Cys Asp Cys Pro Asn Gly Pro Trp Val Trp
                 85              90              95
Leu Pro Ala Phe Cys Gln Ala Ile Gly Trp Gly Asp Pro Ile Thr Tyr
                 100             105             110
Trp Ser His Gly Gln Asn Gln Trp Pro Leu Ser Cys Pro Gln Tyr Val
             115             120             125
Tyr Gly Ser Ala Thr Val Thr Cys Val Trp Gly Ser Ala Ser Trp Tyr
     130             135             140
Ala Ser Thr Ser Gly Arg Asp Ser Lys Ile Asp Val Trp Ser Leu Val
145             150             155             160
Pro Val Gly Ser Ala Thr Cys Thr Ile Ala Ala Leu Gly Ser Ser Asp
                 165             170             175
Arg Asp Thr Val Pro Gly Leu Ser Glu Trp Gly Ile Pro Cys Val Thr
             180             185             190
Cys Val Leu Asp Arg Arg Pro Ala Ser Cys Gly Thr Cys Val Arg Asp
     195             200             205
Cys Trp Pro Glu Thr Gly Ser Val Arg Phe Pro Phe His Arg Cys Gly
     210             215             220
Val Gly Pro Arg Leu Thr Lys Asp Leu Glu Ala Val Pro Phe Val Asn
225             230             235             240
Arg Thr Thr Pro Phe Thr Ile Arg Gly Pro Leu Gly Asn Gln Gly Arg
                 245             250             255
Gly Asn Pro Val Arg Ser Pro Leu Gly Phe Gly Ser Tyr Ala Met Thr
             260             265             270
Arg Ile Arg Asp Thr Leu His Leu Val Glu Cys Pro Thr Pro Ala Ile
     275             280             285
Glu Pro Pro Thr Gly Thr Phe Gly Phe Phe Pro Gly Thr Pro Leu
     290             295             300
Asn Asn Cys Met Leu Leu Gly Thr Glu Val Ser Glu Ala Leu Gly Gly
305             310             315             320
Ala Gly Leu Thr Gly Gly Phe Tyr Glu Pro Leu Val Arg Arg Cys Ser
                 325             330             335
Glu Leu Met Gly Ser Arg Asn Pro Val Cys Pro Gly Phe Ala Trp Leu
             340             345             350
Ser Ser Gly Arg Pro Asp Gly Phe Ile His Val Gln Gly His Leu Gln
     355             360             365
Glu Val Asp Ala Gly Asn Phe Ile Pro Pro Arg Trp Leu Leu Leu
370             375             380
Asp Phe Val Phe Val Leu Leu Tyr Leu Met Lys Leu Ala Glu Ala Arg
385             390             395             400
Leu Val Pro Leu Ile Leu Leu Leu Trp Trp Trp Val Asn Gln Leu
                 405             410             415
Ala Val Leu Gly Leu Pro Ala Val Glu Ala
                 420             425
```

ANTIBODIES AGAINST HEPATITIS G VIRUS AND THEIR USE FOR THE DIAGNOSTIC DETECTION OF HGV AND AS A THERAPEUTIC AGENT

The present invention concerns antibodies against hepatitis G viruses and fragments thereof. The invention in addition concerns a conjugate which contains this antibody or an antibody fragment coupled to a biological molecule. Finally the present invention concerns the use of the antibody for the diagnostic detection of hepatitis G viruses and cell cultures.

In addition to hepatitis A virus (HAV) and hepatitis B virus (HBV) which have been known for a long time, further hepatitis-associated viruses have been characterized recently which belong to various virus families. They cause a number of quite different diseases some of which are very serious so that a differential diagnosis which is as early and unequivocal as possible is highly desirable. The hepatitis viruses are usually named by allocating a consecutive letter of the alphabet. Alternatively new hepatitis-associated viruses can also be named by exclusion of the known viruses. Thus hepatitis C virus (HCV) is also referred to as nonA/nonB hepatitis virus (Choo et al., Science 244 (1989), 359–362). The present invention concerns a virus which cannot be allocated to any of the virus families represented by HAV, HBV, HDV and HEV. The available information about this new virus suggests that it belongs, like HCV, to the family of *flaviviridae* [Chambers et al., Annu. Rev. Microbiol. 44 (1990), 649–688]. However, these data also clearly indicate that it differs significantly from HCV and thus belongs to its own virus group. Therefore this new virus is referred to as hepatitis G virus (HGV) (Linnen et al., Science 271 (1996), 505–508).

A hepatitis-associated virus is described in WO94/18217 which cannot be assigned to any of the groups HAV, HBV, HCV, HDV and HEV. However, the nucleotide sequence of this virus does not have any similarity to the sequence described in the present invention.

The nucleic acid and amino acid sequence of HGV is described in WO95/21922. The recombinant expression of HGV polypeptides in *E. coli* is disclosed in the examples 13, 19 and 20. Explicit reference is made to the sequences disclosed in this application.

The nucleic acid and amino acid sequence of HGV is also described in WO95/32291. The recombinant expression of HGV in *E. coli*, in insect cells and in vaccinia is disclosed in example 16. Explicit reference is made to the sequences disclosed in this application.

Viral infections are usually detected by the presence of antigens and/or antibodies against these antigens in body fluids such as blood serum. Antibodies are required to detect the antigens in an immunoassay which specifically detect the viral antigens. In order to carry out such an immunological test it is also necessary to provide suitable antibodies in an adequate amount.

New processes for the production of HGV antigens and their use for the diagnostic detection of HGV are known from the German Patent Application 196 13 406.4.

This state of the art provides new processes for the expression of HGV antigens. Suitable HGV antigens in this sense are polypeptides from the HGV genome which have at least one antigenic and/or immunogenic determinant. The DNA sequence regions of the HGV total genome are preferred which code for the putative envelope proteins E1 and E2. These envelope proteins are composed of an amino-terminal main section which is located on the outside of a functional virus particle and plays a decisive role when it docks with the host organism and a short carboxy-terminal hydrophobic section which is anchored in the membrane.

The above-mentioned patent application also discloses a recombinant cell which presents HGV antigens on its surface in a membrane-bound form, in particular the antigens E1 or/and E2 or immunologically relevant partial sequences thereof.

This cell can be used as a diagnostic reagent for the detection of HGV e.g. by FACS analysis or by ELISA. For this the reaction of a cell, which presents a HGV antigen on its surface, with a sample liquid e.g. human serum is determined. If a reaction occurs it can be assumed that anti-HGV antibodies are present in the tested sample.

However, there are still no antibodies against the HGV epitopes.

Classically antibodies are obtained by immunizing mice or other animals with antigens. Monoclonal antibodies, which have the advantage of unlimited production and exactly defined specificity, can then be selected from the at first polyclonal pool by hybridoma technology (Köhler and Milstein, Nature 256 (1975), 495). For this myeloma cells are fused with spleen cells of the immunized animal.

It was therefore the object of the present invention to produce a—preferably monoclonal—antibody against a HGV surface antigen in particular against the envelope protein E2 of HGV. A further object of the invention was to use this antibody as a diagnostic reagent for the detection of HGV.

The invention provides monoclonal and polyclonal antibodies against HGV surface antigens.

In addition a monoclonal or polyclonal antibody against the HGV E2 surface antigen is provided.

Suitable immunogens for obtaining the antibodies are polypeptides and in particular surface antigens from the HGV genome (WO95/21922 and WO95/32291) or partial peptide sequences thereof which have at least one antigenic or/and immunogenic determinant. The putative envelope protein E2 or an antigenic or/and immunogenic partial peptide section thereof is particularly preferred and especially a partial peptide section from the amino-terminal region. The putative envelope protein E1 or/and an antigenic or immunogenic partial peptide section thereof is also suitable as an immunogen which in particular is derived from the amino-terminal region. Immunization methods using viral envelope proteins are known cf. HBsAg (Michel et al., Bio/Technology 3 (1985), 561–566) and E2/NS1 of HCV (Lesniewski et al., J. Med. Virol. 45 (1995), 415–422).

However, the antibodies according to the invention are particularly preferably produced by a multistep immunization process which includes a DNA immunization (Davies et a., Ann., N.Y. Acad. Sci. 772 (1995), 21–29). In this manner it is possible to present to the animal's immune system the surface antigens in a form that is as authentic as possible i.e. in a form that is preferably correctly post-translationally processed and optionally glycosylated and exported from the cell. In the first step of the immunization process according to the invention the DNA sequence coding for the immunization antigen is cloned into a eukaryotic expression vector and this construct is injected directly into a suitable tissue of the experimental animal (e.g. mouse, rat, rabbit etc.) such as the skeletal muscle. The DNA sequence coding for the antigen is located on the expression vector under the control of a promoter which is known to be active in the tissue of the appropriate experimental animal that is used in each case.

It is particularly preferable to clone a DNA sequence coding for the envelope protein E2 or a section thereof in an expression vector such as pcDNA3 in the correct reading frame next to DNA sequences coding for an amino terminal signal peptide and optionally for a marker epitope e.g. the so-called FLAG epitope and to express it together with the two elements as a fusion protein. The signal sequence can for example be the erythropoietin signal sequence (Jacobs et al., Nature 313 (1985), 806–810). The FLAG epitope is an octapeptide (Hopp et al., Bio/Technology 6 (1988), 1204–1210) against which a monoclonal antibody is commercially available which can be used to identify and optionally to purify the desired expression product.

When the antigen is expressed in the tissue of-the experimental animal the protein biosynthesis takes place on the ribosomes in the cytosol. When the HGV antigens are expressed in operative linkage with amino-terminal signal sequences e.g. 20 to 30 amino acid long hydrophobic sequences which are recognized during protein biosynthesis in the cytosol by so-called signal recognition particles, the ribosomes are directed to the endoplasmic reticulum (ER). Here the polypeptide chains are channelled through the ER membrane until they are arrested in the membrane by stop transfer sequences. The proteins are optionally glycosylated in the lumen of the ER and subsequently further modified in the Golgi apparatus. Finally they are sorted for export in the direction of the plasma membrane. In this manner the antigen is presented to the immune system in as authentic form as possible and can lead to the formation of high quality anti-HGV antibodies.

The immunization process according to the invention preferably also includes a booster immunization in which eukaryotic cells which express the corresponding HGV surface antigen on their membranes are injected into the experimental animal. Reference is made to DE 196 13 406.6 with regard to the production of such cells.

Polyclonal antibody compositions or monoclonal antibodies against HGV surface antigens can then be isolated from the immunized experimental animal. In order to produce a polyclonal antibody composition that is specific for HGV the serum is preferably purified e.g. an affinity chromatography is carried out over a column coated with the appropriate antigen e.g. the E2 antigen.

In order to obtain monoclonal antibodies use is made of the hybridoma technology of Köhler and Milstein or subsequent developments thereof. Suitable antibody-producing hybridoma cells can for example be produced by fusing spleen cells from the immunized animals with myeloma cells according to Galfre and Milstein, Meth. Enzymol. 73 (1981), 3–46. The primary cultures of the fusion cells are then tested for the synthesis of specific antibodies. Specific primary cultures can be cloned in microtitre plates by means of fluorescence activated cell sorting (FACS).

Hence the invention concerns a polyclonal or monoclonal antibody against a hepatitis G virus surface antigen which can be produced by a process which comprises the following steps:

Immunization of experimental animals with an expression vector comprising: a promoter, a eukaryotic signal sequence, a DNA sequence coding for the hepatitis G virus surface antigen and optionally a marker sequence, optionally a booster immunization of the experimental animals with cells which express the HGV surface antigen on their membranes and obtaining polyclonal or monoclonal antibodies that are specific for the hepatitis G virus surface antigen from the immunized experimental animal.

The antibody against the HGV E2 surface antigen which is provided is preferably directed against a polypeptide which is coded by (a) the nucleotide sequence between position 127 and 1290 shown in SEQ ID NO.1, (b) a sequence corresponding to the sequence from (a) within the scope of the degeneracy of the genetic code or/and (c) a nucleotide sequence hybridizing with the sequences from (a) or/and (b) under stringent conditions.

A further characteristic of the antibody against the HGV E2 surface antigen is that it is directed against a polypeptide which comprises (a) the amino acid sequence between position 39 and 426 shown in SEQ ID NO.2 or (b) an amino acid sequence which is at least 80% homologous with the sequence from (a).

In addition hybridoma cell lines are provided which produce monoclonal anti-E2 antibodies according to the invention. These hybridoma cell lines were deposited according to the rules of the Budapest Contract at the "Deutsche Sammlung von Mikroorganismen und Zellkulturen GmbH (DSMZ)", Mascheroder Weg 1b, D-38124 Braunschweig. The depository data are as follows:

| clone 11 | DSM ACC 2280 | 19.09.1996 |
| clone 17 | DSM ACC 2284 | 24.09.1996 |
| clone 30 | DSM ACC 2285 | 24.09.1996 |

The invention also concerns a monoclonal antibody obtainable from the cell lines stated above as well as antibodies with an equivalent binding specificity which preferably recognize the same epitope as the deposited antibodies.

In addition the invention concerns any fragment of one of the antibodies described above.

Yet a further subject matter of the present invention is a conjugate which contains one of the antibodies described above or a corresponding antibody fragment which is coupled to a biological molecule.

In a preferred embodiment the biological molecule in the conjugate comprises a marker group. All known marker groups come into consideration as a marker group which can be detected in a test system i.e. directly or indirectly detectable marker groups. A directly detectable marker group is understood as a group which generates a directly detectable signal e.g. a radioactive group, an enzyme group or a luminescent group. Enzyme groups and luminescent groups are particularly preferred and in particular electrochemiluminescent groups. On the other hand the marker group can also be an indirectly detectable group e.g. a biotin or hapten group which can be detected by reaction with a suitable binding partner (streptavidin, avidin or anti-hapten antibody) which in turn carries a signal-generating group. Hapten or biotin groups can also be used as solid phase binding groups to immobilize the antibodies on a solid phase. The marker and solid phase binding group can be coupled to the antibody in a known manner.

A further subject matter of the invention concerns the use of the antibodies as diagnostic reagents for the detection of HGV e.g. by FACS analysis or by ELISA. For this the reaction of the antibodies with a sample liquid, e.g. human serum, is determined. If a reaction occurs it can be assumed that HGV antigens are present in the tested sample.

For use in a diagnostic test the antibodies are preferably provided with at least one marker group or solid phase binding group as described above.

The detection of HGV is carried out in particular by the immunological determination of HGV antigens in a sample liquid wherein the sample liquid is incubated with at least one antibody according to the invention and the binding is detected. This immunological method of determination can be carried out according to any known test format e.g. in a homogeneous immunoassay with a single reaction phase or in a heterologous immunoassay with more than one reaction phase. A heterogeneous test format is preferably used in which the presence of the antigen is detected in the presence of a solid phase.

One embodiment of this test format is the so-called bridge test (see example 5). In this embodiment the sample liquid is incubated with at least two antibodies A1 and A2 according to the invention in which A1 is bound to a solid phase or is present in a form capable of binding to a solid phase (so-called capture antibody) and A2 carries a marker group (so-called detection antibody). The antigen in the sample liquid is detected by determining the label in the solid phase or/and in the liquid phase, preferably in the solid phase, via an immobilized, i.e. a solid phase-bound immune complex. The test procedure preferably comprises mixing of the sample liquid with a labelled A2 as well as with A1 bound to or capable of binding to a solid phase in order to obtain a labelled immobilized complex of labelled antibody, antigen and solid phased antibody.

A further area of application for the antibodies according to the invention is a therapeutic application. For this the antibodies according to the invention are preferably produced in a purified form and then formulated as injectable liquids which can be solutions or suspensions. Further components are for example water, salt solutions, glucose or glycerol. The antibodies can also be enclosed in liposomes. The antibodies are usually administered parenterally by injection preferably subcutaneously or intramuscularly.

The present invention is described in more detail by the following examples, sequence protocols and figures, wherein:

SEQ ID NO. 1: shows a DNA nucleotide sequence which codes for HGV-E2 plus an amino terminal fusion part SEQ ID NO. 2: shows an amino acid sequence of HGV-E2 plus an amino terminal fusion part

EXAMPLES

Example 1

Cloning of the Expression Construct HGV-E2

Figure 1:
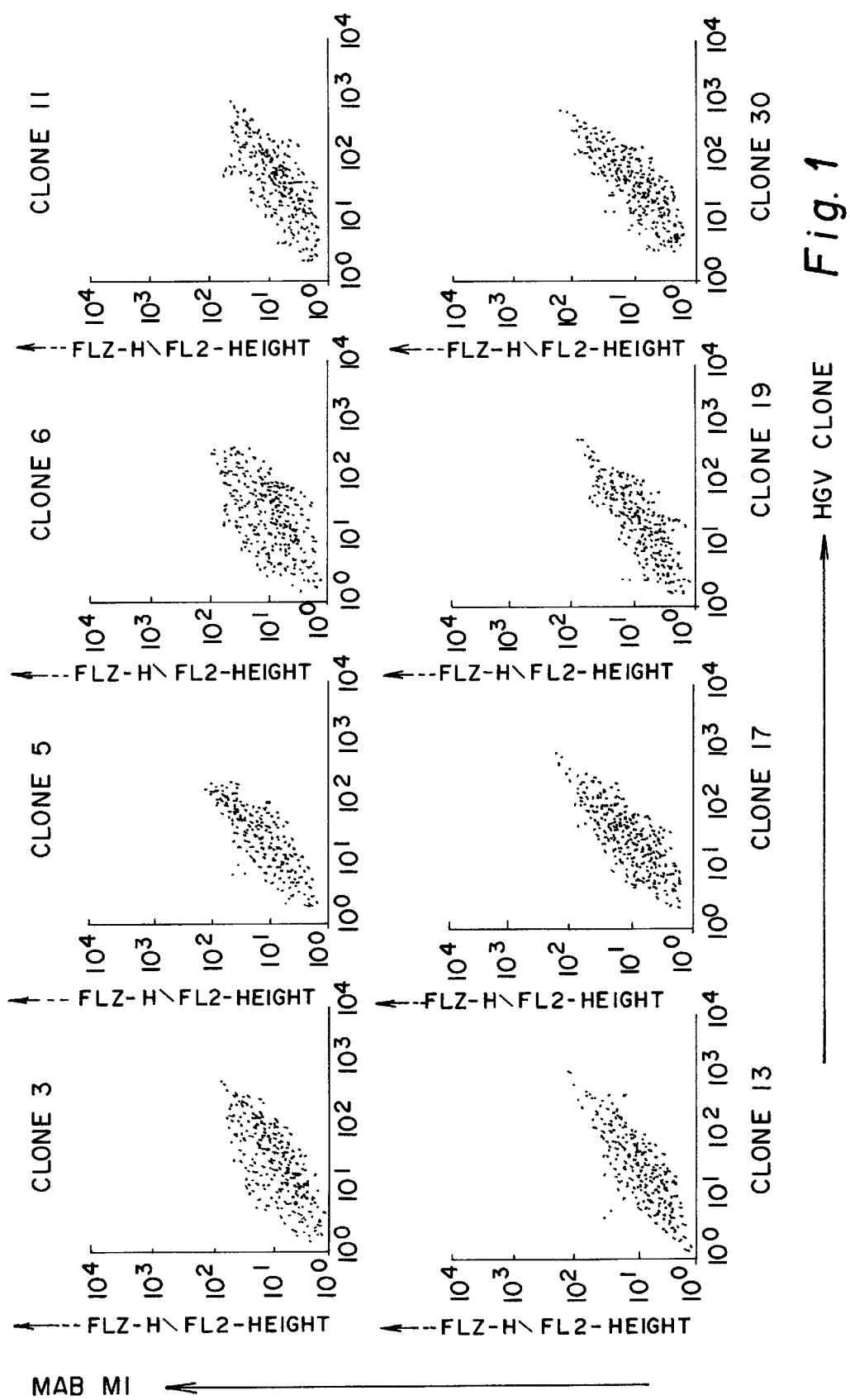
FIG. 1: staining of CHO cells that express FLAG-E2 with anti-FLAG-M1 and anti-E2 MABs 3, 5, 6, 11, 13, 17, 19, 30

Standard methods were used to manipulate the DNA such as those described by Sambrook et al. (1989) in Molecular cloning: A Laboratory Manual, Cold Spring Harbor Laboratory, New York and Ausubel et al., (1989) in Current Protocols in Molecular Biology, John Wiley & Sons, New York.

The manipulation of the DNA was carried out in the *E. coli* K12 strain DH5α.

A derivative of the vector pcDNA3 with a CMV promoter and BGH poly-adenylation signal (Invitrogen BV, NV Leek, Netherlands) was used as the expression vector for the DNA immunization. For this the vector pcDNA3 was modified by substituting the neomycin resistance gene by a dehydrofolate reductase (DHFR) gene. This was carried out by restriction cleavage of pcNDA3 with AvrII/Bst1107I, isolation of the ca. 4 kBp long vector fragment and insertion of a ca. 700 Bp long AvrII/-Bst1107I DHFR fragment [Setzer et al. (1982) J. Biol. Chem. 257, 5143–5147; Crouse et al. (1982) J. Biol. Chem. 257, 7887–7897].

The DNA sequence coding for the envelope protein E2 was cloned into the resulting vector pcDNA3-DHFR in operative linkage to a signal peptide sequence as well as to a DNA sequence coding for a so-called FLAG epitope. The erythropoietin signal sequence [Jacobs et al. (1985) Nature 313, 806–810] was used as the signal sequence as a 93 Bp long EcoRI/EheI fragment (position 1 to 93 of SEQ ID NO.1). The FLAG epitope is a short octapeptide [Hopp et al. (1988) Bio/Technology 6, 1204–1210] against which a monoclonal antibody anti-Flag-M1 (Kodak Eastman) is available which can be used to purify and identify the desired expression product. Two oligonucleotides were hybridized to each other to prepare the DNA sequence coding for the FLAG epitope and used as a linker after treatment by kinase (corresponding to position 94–126 of SEQ ID No. 1).

In order to produce the E2 expression vector, the plasmid pcDNA3-DHFR was digested with EcoRI and NotI and the ca. 5.9 kBp long vector fragment was isolated and ligated in a 3-way ligation with the EcoRI/EheI signal sequence fragment and the FLAG linker.

The HGV cDNA that was used was derived from Genelabs Technologies Inc., Redwood City, Calif., USA (WO 95/32291). The almost complete HGV genome was present as a ca. 9.3 kBp long XbaI/EcoRI fragment which had been cloned into the corresponding restriction sites of the vector pGEM-3Z (Promega Corp., Madison, Wis., USA). The DNA sequences coding for E2 (position 127–1290 of SEQ ID NO.1) were amplified by means of PCR using suitable oligonucleotides and cloned as NotI/XbaI fragments in frame next to the DNA sequences coding for the signal peptide and FLAG epitope.

Example 2

Production of Monoclonal Antibodies Against HGV-E2

2.1. DNA Immunization

Female BALB/c mice were used for the immunization. In order to increase the efficiency of DNA uptake which should be about ten-fold higher in regenerating muscle than in untreated muscle, the animals were treated with the snake venom Latoxan (Rosans, France) before the first immunization. For this the mouse was injected in each case with 80 μl of a 10 μM solution of the venom in both tibial muscles. Five days later the immunization was started, each mouse was injected five times (week 0, 5, 10, 11, 12) with plasmid DNA. In this process 50 μg DNA was injected into each tibial muscle i.e. 100 μg per animal and immunization. The plasmid DNA was purified over a Qiagen column according to the manufacturer's instructions.

The animals were boostered before removing the spleen in week 20. For this purpose $10^7$ CHO cells which expressed HGV-E2 on their membranes were injected intravenously into each animal.

2.2 Fusion and Cloning

Spleen cells of the immunized mice were fused with myeloma cells following the procedure of Galfré and Milstein (1981) Meth. Enzymol. 73, 3-46. In this process ca. $10^8$ spleen cells of the immunized mouse were mixed with $2 \times 10^7$ myeloma cells (P3X63-Ag8-653, ATCC CRL1580) and centrifuged. The cells were then washed once in RPMI 1640 medium w/o FCS and again centrifuged at 400 g. The supernatant was discarded, the cell sediment was gently loosened by tapping, 1 ml PEG (molecular weight 4000, Life Technologies, Cat. No. 14030035) was added to this within one minute and mixed with the cells by gently swirling in a 37° C. warm water bath. Subsequently 5 ml RPMI 1640 medium w/o FCS was added dropwise within 5 min and mixed in a 37° C. warm water bath by continuous swirling. After the addition of 25 ml RPMI 1640 medium w/o FCS the cells were centrifuged for 10 min at 400 g. The cell pellet was taken up in RPMI 1640 medium, 10% FCS and inoculated into hypoxanthine azaserine selection medium (100 mmol/l hypoxanthine, 1 µg/ml azaserine in RPMI 1640, 10% FCS). Interleukin 6 (Boehringer Mannheim, Cat. No. 1444 581) was added to the medium as a growth factor. After ca. 10 days the primary cultures were tested for the synthesis of E2-specific antibodies (see example 3). E2-specific primary cultures were cloned in microtitre plates by means of fluorescence activated cell sorting (FACS). For this purpose interleukin 6 was added to the medium as a growth additive. The purification of the antibodies from the ascites fluid of mice and the derivatization with biotin or digoxigenin was carried out according to standard methods in protein chemistry.

Example 3

Determination of the Specificity of the Produced Antibodies

In order to determine the specificity of the antibodies in the culture supernatant of the hybridoma cells the reactivity with CHO cells which expressed on their membranes either the FLAG-E2 fusion protein or the human urokinase receptor, which is also provided with an $NH_2$-terminal FLAG sequence, was detenined in two parallel ELISA experiments. For this the cells were inoculated at a density of ca. $4\times10^4$ per well of a microtitre plate on the day before the experiment. On the next day unspecific binding sites were firstly blocked by a two hour incubation with 200 µl RPMI 1640 medium, 10% FCS, 1% BycoC per well. Subsequently 100 µl of the cell culture supernatants was pipetted into each well and incubated for 60 min at room temperature. After washing three times with Dulbecco's PBS, 0.02% Tween 20, anti-mouse IgG-peroxidase Fab fragment (Boehringer Mannheim Cat. No. 1500 686) was added to the cells in a volume of 100 µl and a concentration of 50 mU/ml. After 60 min incubation at room temperature and washing three times with Dulbecco's PBS, 0.02% Tween 20, ABTS® was used as a substrate and the colour change was measured in an ELISA reader at 405/490 nm after 30–60 min.

A total of 8 hybridoma clones were identified (anti-HGV-E2 clones 3, 5, 6, 11, 13, 17, 19, 30) whose monoclonal antibodies specifically recognize CHO cells expressing EGV-B2 (MABs 3, 5, 6, 11, 13, 17, 19, 30).

Example 4

FACS Analysis with CHO Cells that Express HGV-E2

In this method CHO cells which express the FLAG E2 fusion protein on their membranes were stained successively with one of the E2-specific MABs and the anti-FLAG-M1. Since both epitopes are located on one molecule this experiment gives information about possible epitope overlaps and thus about the influence of the FLAG epitope on the binding of E2-specific antibodies.

The cells were detached from the culture vessel with 0.02% EDTA in PBS and washed in PBS. $2\times10^5$ cells were resuspended in each case in 100 µl Dulbeccol's PBS, 0.2% bovine serum albumin, 0.02% $NaN_3$ and incubated for 15 min on ice with the MABs 3, 5, 6, 11, 13, 17, 19 or 30 (2 µg/ml each case), washed twice with the same buffer and incubated for a further 15 min with anti-mouse Ig-fluorescein $(Fab')_2$ fragment (Boehringer Mannheim, Cat. No. 1295 750). After washing twice, the cells were incubated for 15 min on ice with mouse IgG (Sigma) at a concentration of 10 µg/ml to block the free anti-mouse IgG binding sites. Subsequently biotinylated anti-FLAG-M1 was added to the mixture at a concentration of 0.35 µg/ml. After incubating for 15 min. on ice it was washed twice and the second MAB labelled fluorescently this time with streptavidin-R-phycoerythrin (Boehringer Mannheim, Cat. No. 1428 560) was added for 15 min on ice. After washing twice, the cells were analysed in a flow cytometer (FIG. 1). The double staining resulted in each case in a straight line with a different gradient. A gradient of 45° which is the case for the MABs 5, 17 and 30 is typical for the recognition of two independent epitopes. A gradient that differs from 45° such as in the case of the MABs 3, 11, 13 and 19 could indicate a mutual steric hindrance of the binding.

Figure 2:
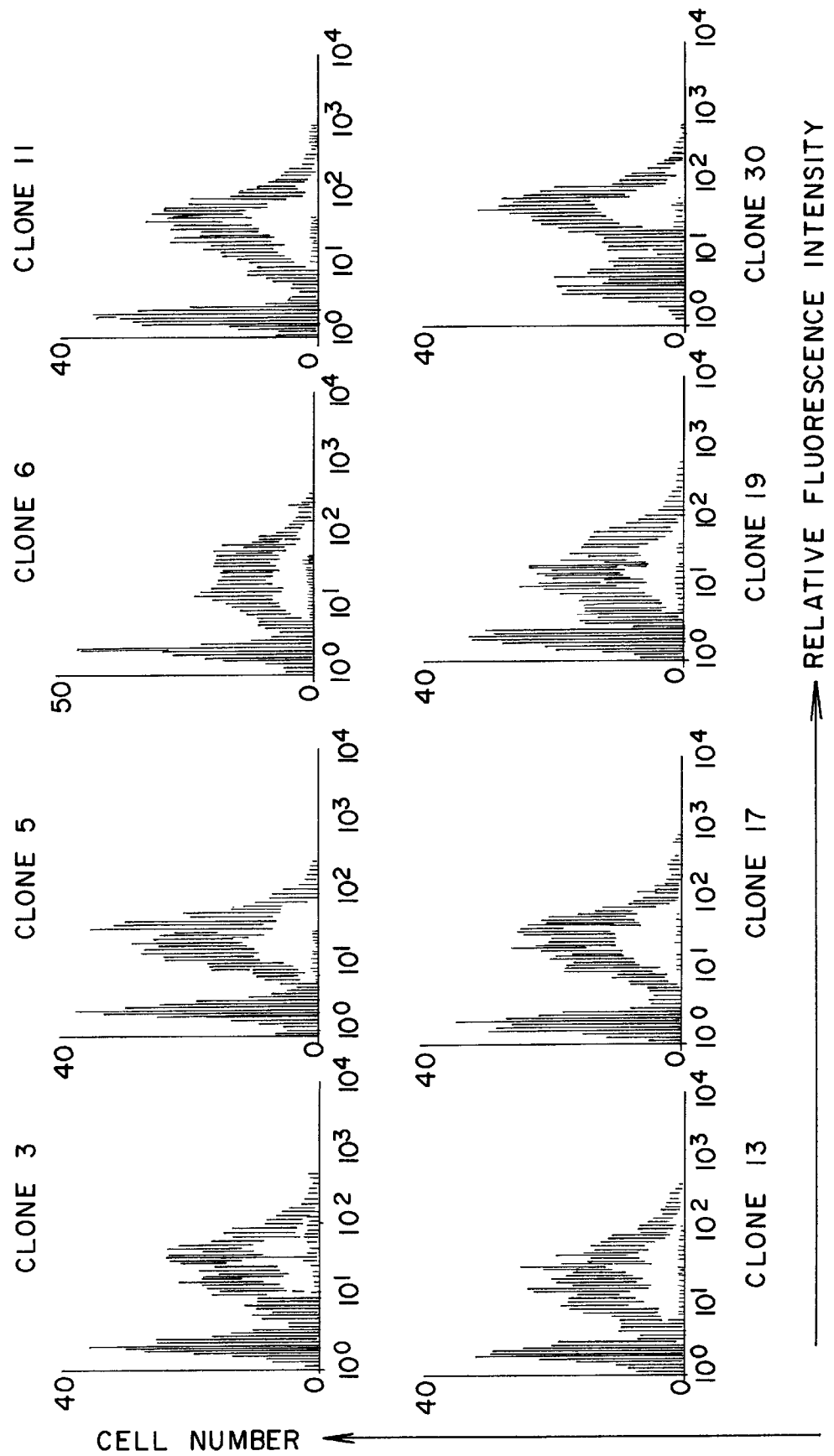
FIG. 2: staking of CHO cells (filled in area) and CHO cells expressing FLAG-E2 (open area) with the anti-E2 MABs 3, 5, 6, 11, 13, 17, 19, 30.

In order to exclude an unspecific binding of the anti-E2-MABs to CHO cells, additional CHO cells were also stained as a negative reference. In this case the staining with anti-FLAG-M1 was omitted (FIG. 2). In this case only MAB 30 exhibited a slight unspecific reaction with CHO cells whereas no background staining was detectable for the other seven MABS.

Example 5

Examination of Epitope Overlapping

The test was carried out as a bridge test using isolated HGV-E2 as the antigen to characterize the E2-specific MABs. The antigen was bound via a biotinylated E2-specific capture antibody which in turn was coupled to a streptavidin-coated ELISA plate.

a) Preparation of the ELISA Plates:

Streptavidin-coated ELISA microtitre plates (Microcode, streptavidin MTP F8) were incubated for 60–120 min with 50 µl biotinylated MAB (2 µg/ml in Dulbecco's PBS, 0.2% bovine serum albumin) and subsequently washed three times with 0.9% NaCl, 0.05% Tween 20.

b) Cell Lysis:

The cells expressing HGV-E2 were detached from the culture vessel with 0.02% EDTA in PBS and washed in PBS. Subsequently the cells were lysed in PBS, 0.5% Nonidet P 40, protease mix (Boehringer Mannheim, Cat. No. 1206 893). For this $10^7$ cells/ml solubilization solution were incubated in each case for two hours on ice. Undissolved material was separated by centrifugation.

c) Coupling of the Antigens and Assay:

The ELISA plates prepared according to a) were incubated for 60 min at room temperature with the cell lysate (diluted in PBS, 0.1% Nonidet P40). After washing three times with PBS, 0.1% Nonidet P40 the second MAB which was labelled this time with digoxigenin was added and incubated for 90 min at room temperature. After washing several times with PBS, 0.1% Nonidet P40 it was subsequently incubated for one hour with anti-digoxigenin IgG-POD. After washing intensively with PBS, 0.1% Nonidet P40 ABTS® was added as a substrate and the colour change was measured in an ELISA reader at 405/490 nm after 30–60 min.

The MABs 3, 5, 11, 13, 17, 19, 30 were used in all possible combinations as biotinylated capture antibodies and used as digoxigenin-labelled detection antibodies. Since in the ELISA format described above all reaction steps proceed sequentially, a low dissociation constant is essential for a good capture antibody. This prerequisite is fulfilled by the MABs 5, 11, 17 and 30. In contrast the MABs 3, 13 and 19 can only be used as detection antibodies. The simultaneous use of a MAB as a capture and detection antibody was not possible in this test which indicates a monovalent conformation of the antigen.

The test also enables a possible epitope overlap of the individual MABs to be examined. Apparently the MABs 5 and 17 recognize the same epitope since this combination did not lead to a signal in the bridge test. In contrast the MABs 5 and 17 did not compete with the MABs 11 or 30. This shows that at least three different epitopes on HGV-E2 are recognized by these MABs.

---

We claim:

1. A cell culture with the depositary number DSM ACC2280.

2. A cell culture with the depositary number DSM ACC2284.

3. A cell culture with the depositary number DSM ACC2285.

4. An antibody against a hepatitis G virus surface antigen, wherein said antibody is obtained from the cell line DSM ACC 2280 or binds to the same epitope as an antibody obtained from the cell line DSM ACC 2280.

5. An antibody against a hepatitis G virus surface antigen, wherein said antibody is obtained from the cell line DSM ACC 2284 or binds to the same epitope as an antibody obtained from the cell line DSM ACC 2284.

6. An antibody against a hepatitis G virus surface antigen, wherein said antibody is obtained from the cell line DSM ACC 2285 or binds to the same epitope as an antibody obtained from the cell line DSM ACC 2285.

* * * * *